(12) United States Patent
Zhi et al.

(10) Patent No.: US 9,326,991 B2
(45) Date of Patent: May 3, 2016

(54) NUCLEOTIDE PRODRUG COMPOUNDS AND USE

(71) Applicant: LIGAND PHARMACEUTICALS INC., La Jolla, CA (US)

(72) Inventors: Lin Zhi, La Jolla, CA (US); K. Raja Reddy, La Jolla, CA (US)

(73) Assignee: LIGAND PHARMACEUTICALS, INC., San Diego, CA (US)

(*) Notice: Subject to any disclaimer, the term of this patent is extended or adjusted under 35 U.S.C. 154(b) by 30 days.

(21) Appl. No.: 14/428,151

(22) PCT Filed: Sep. 12, 2013

(86) PCT No.: PCT/US2013/059507
§ 371 (c)(1),
(2) Date: Mar. 13, 2015

(87) PCT Pub. No.: WO2014/043380
PCT Pub. Date: Mar. 20, 2014

(65) Prior Publication Data
US 2015/0246068 A1    Sep. 3, 2015

Related U.S. Application Data

(60) Provisional application No. 61/701,104, filed on Sep. 14, 2012.

(51) Int. Cl.
| | | |
|---|---|---|
| C07H 19/12 | (2006.01) |
| C07F 9/6574 | (2006.01) |
| A61K 31/7056 | (2006.01) |
| A61K 45/06 | (2006.01) |

(52) U.S. Cl.
CPC ............ *A61K 31/7056* (2013.01); *A61K 45/06* (2013.01); *C07F 9/65742* (2013.01); *C07H 19/12* (2013.01)

(58) Field of Classification Search
None
See application file for complete search history.

(56) References Cited

U.S. PATENT DOCUMENTS

| 6,312,662 B1 | 11/2001 | Erion et al. |
| 6,321,662 B1 * | 11/2001 | Fraise .............................. 108/25 |

FOREIGN PATENT DOCUMENTS

WO    WO 99/45016 A2    9/1999

OTHER PUBLICATIONS

Erion, Mark D. et al., "Preparation of cyclic nucleotides as FBPase inhibitor prodrugs" retrieved from STN Database accession No. 1999:576934.
Erion, Mark D. et al., "Prodrugs phosphorus-containing compounds and pharmacodynamics action", XP002717889.

* cited by examiner

*Primary Examiner* — Traviss C McIntosh, III
(74) *Attorney, Agent, or Firm* — Knobbe, Martens, Olson & Bear LLP

(57) ABSTRACT

Embodiments of the present invention include nucleoside 5'-monophosphate derivative compounds, their preparation and their uses. In some embodiments, nucleoside 5'-monophosphate derivative compounds are useful to treat viral infections.

22 Claims, No Drawings

NUCLEOTIDE PRODRUG COMPOUNDS AND USE

RELATED APPLICATIONS

This application is the U.S. National Phase of International Application No. PCT/US2013/059507 entitled "NOVEL NUCLEOTIDE PRODRUG COMPOUNDS AND USE", filed Sep. 12, 2013 and published in English on Mar. 20 2014 as WO 2014/059507 which claims the benefit of U.S. Provisional App No. 61/701,104 filed Sep. 14, 2012 entitled "NOVEL NUCLEOTIDE PRODRUG COMPOUNDS AND USE" which are each incorporated herein by reference in its entirety.

FIELD OF THE INVENTION

Embodiments of the present invention include nucleoside 5'-monophosphate derivative compounds, their preparation and their uses. In some embodiments, nucleoside 5'-monophosphate derivative compounds are useful to treat viral infections.

BACKGROUND OF THE INVENTION

Hepatitis is a viral disease that causes inflammation of the liver that may lead to cirrhosis, primary liver cancer and other long-term complications. Nucleosides are a well-recognized class of compounds shown to be effective against a variety of viral infections, including hepatitis B, HIV, and herpes. Several nucleosides are reported to inhibit hepatitis C (HCV) virus replication, including ribavirin, which currently is marketed as a drug combination with various interferons, and the direct acting antiviral agents.

Nucleosides are generally effective as antiviral agents following conversion to the corresponding nucleoside 5'-triphosphate (NTP). Conversion occurs inside cells through the action of various intracellular kinases. The first step, i.e. conversion of the nucleoside to the 5'-monophosphate (NMP) is generally the slow step and involves a nucleoside kinase, which is encoded by either the virus or host. Conversion of the NMP to the NTP is generally catalyzed by host nucleotide kinases. The NTP interferes with viral replication through inhibition of viral polymerases and/or via incorporation into a growing strand of DNA or RNA followed by chain termination.

Use of synthetic nucleosides to treat viral liver infections is often complicated by several problems. In some cases, the desired nucleoside is a good kinase substrate and accordingly produces NTP in the liver as well as other cells and tissues throughout the body. Since NTP production is often associated with toxicity, nucleoside antiviral efficacy can be limited by extrahepatic toxicities. In other cases, the desired nucleoside is a poor kinase substrate which is not efficiently converted into the NMP and ultimately into the NTP. Many nucleosides have poor oral bioavailability and need to be in a prodrug form for oral use.

Ribavirin is orally available and is likely to be absorbed via a group of transporters, which may increase the likelihood of undesirable drug-drug interaction. In human subjects, Ribavirin has a relatively long half-life (~12 days) and may be sequestered in cells, such as red blood cells, causing anemia and other side effects. Indeed, ribavirin may be sequestered in red blood cells as long as 6-months, namely, the average lifespan of the cells.

A strategy of selectively delivering ribavirin monophosphate into the liver via a transporter independent mechanism would be beneficial to patients who suffer from viral liver diseases due to an increase in the liver concentration of the biologically active ribavirin phosphates, a decrease in concentration of ribavirin outside the liver, and potentially an increase in efficacy in patients having ribavirin transporter deficiency. For example, U.S. Pat. No. 6,312,662 disclose the use of certain phosphate prodrugs for the liver-specific delivery of various drugs including nucleotides for the treatment of patients with liver diseases such as hepatitis C, hepatitis B and hepatocellular carcinoma.

SUMMARY OF THE INVENTION

Embodiments of the present invention include nucleoside 5'-monophosphate derivative compounds, their preparation and their uses. In some embodiments, nucleoside 5'-monophosphate derivative compounds are useful to treat viral infections.

Some embodiments of the compounds, compositions and methods provided herein include a compound of Formula I:

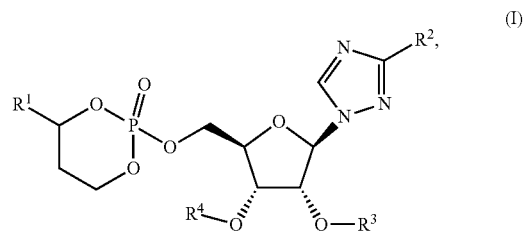

(I)

or a pharmaceutically acceptable salt thereof,
wherein:
$R^1$ is an optionally substituted phenyl or an optionally substituted pyridyl;
$R^2$ is

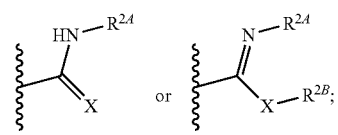

$R^{2A}$ is selected from the group consisting of H (hydrogen), a $C_1$-$C_6$ alkyl, a $C_1$-$C_6$ heteroalkyl, and a $C_1$-$C_6$ acyl;
$R^{2B}$ is selected from the group consisting of H (hydrogen), a $C_1$-$C_6$ alkyl, a $C_1$-$C_6$ heteroalkyl, and a $C_1$-$C_6$ acyl;
$R^3$ and $R^4$ are each independently selected from the group consisting of H (hydrogen), acyl, and heteroacyl; or $R^3$ and $R^4$ can be optionally linked to form a carbonyl; and
X is O (oxygen), S (sulfur) or NH.

In some embodiments, $R^1$ is selected from the group consisting of:

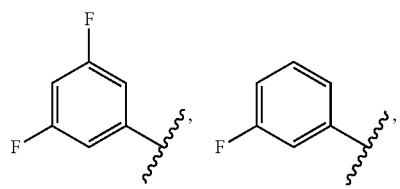

In some embodiments, $R^2$ is

[structure: HN-R^{2A}, C(=X)-]

In some embodiments, X is O (oxygen).

In some embodiments, $R^{2A}$ is selected from the group consisting of H (hydrogen) and $C_1$-$C_6$ alkyl.

In some embodiments, $R^3$ and $R^4$ are each H, or $R^3$ and $R^4$ can be optionally linked to form a carbonyl.

In some embodiments, $R^2$ is

[structure: N-R^{2A}, =C, X-R^{2B}]

In some embodiments, X is O (oxygen).
In some embodiments, $R^{2A}$ is of H (hydrogen).
In some embodiments, $R^{2B}$ is $C_1$-$C_6$ alkyl.
In some embodiments, $R^3$ and $R^4$ are each independently selected from the group consisting of H (hydrogen), acyl, and heteroacyl.

In some embodiments, the compound includes 2R-(3-Aminocarbonyl-1H-1,2,4-triazole)-5R-(4S-(4-pyridinyl)-2-oxo-1,3,2-dioxaphosphorinanyloxymethyl)-3R,4R-dihydroxytetrahydrofuran, 2R-(3-Aminocarbonyl-1H-1,2,4-triazole)-5R-(4R-(4-pyridinyl)-2-oxo-1,3,2-dioxaphosphorinanyloxymethyl)-3R,4R-dihydroxytetrahydrofuran, 2R-(3-Aminocarbonyl-1H-1,2,4-triazole)-5R-(4S-(3-chlorophenyl)-2-oxo-1,3,2-dioxaphosphorinanyloxymethyl)-3R,4R-dihydroxytetrahydrofuran, 2R-(3-Aminocarbonyl-1H-1,2,4-triazole)-5R-(4R-(3-chlorophenyl)-2-oxo-1,3,2-dioxaphosphorinanyloxymethyl)-3R,4R-dihydroxytetrahydrofuran, 2R-(3-Aminocarbonyl-1H-1,2,4-triazole)-5R-(4S-(3-chlorophenyl)-2-oxo-1,3,2-dioxaphosphorinan-2R-yloxymethyl)-3R,4R-dihydroxytetrahydrofuran, 2R-(3-Aminocarbonyl-1H-1,2,4-triazole)-4R-(4S-(3-chlorophenyl)-2-oxo-1,3,2-dioxaphosphorinan-2R-yloxymethyl)-7-oxo-3,6,8-trioxa-cis-bicyclo[3.3.0]octane, 2R-(3-Aminocarbonyl-1H-1,2,4-triazole)-5R-(4S-(3-chlorophenyl)-2-oxo-1,3,2-dioxaphosphorinan-2R-yloxymethyl)-3R,4R-diacetyloxytetrahydrofuran, 2R-(3-(1-Ethoxy-1-iminomethyl)-1H-1,2,4-triazole)-5R-(4S-(3-chlorophenyl)-2-oxo-1,3,2-dioxaphosphorinan-2R-yloxymethyl)-3R,4R-diacetyloxytetrahydrofuran, 2R-(3-Ethylaminocarbonyl-1H-1,2,4-triazole)-5R-(4S-(3-chlorophenyl)-2-oxo-1,3,2-dioxaphosphorinan-2R-yloxymethyl)-3R,4R-diacetyloxytetrahydrofuran, and (2R,3R,4R,5R)-2-(3-Carbamoyl-1H-1,2,4-triazol-1-yl)-5-((((2R,4S)-4-(3-chlorophenyl)-2-oxido-1,3,2-dioxaphosphinan-2-yl)oxy)methyl)tetrahydrofuran-3,4-diyl dipropionate.

Some embodiments of the compounds, compositions and methods provided herein include a pharmaceutical composition comprising a compound provided herein and a pharmaceutically acceptable carrier.

Some embodiments of the compounds, compositions and methods provided herein include a method of treating a viral liver infection comprising administering an effective amount of a compound provided herein to a subject in need thereof.

Some embodiments also include administering an effective amount of a second or multiple therapeutic agents in combination with a compound provided herein to the subject in need thereof In some embodiments, the second or multiple therapeutic agents are selected from the group consisting of thymosin alpha-1, interferon-λ, an inhibitor of HCV protease, an inhibitor of HCV NS5A replication complex, an inhibitor of HCV NS5B polymerase, an inhibitor of HCV helicase, a cyclophilin inhibitor, an inhibitor of inosine monophosphate dehydrogenase, interferon-α, and pegylated interferon-α.

In some embodiments, the second therapeutic agent is interferon-α or pegylated interferon-α, alone or in combination with other antiviral agents.

In some embodiments, the multiple therapeutic agents are other direct acting antivirals.

In some embodiments, the direct acting antivirals are selected from the group consisting of an inhibitor of HCV protease, an inhibitor of HCV NS5A replication complex, a nucleoside-based inhibitor of HCV NS5B polymerase, a non-nucleoside inhibitor of HCV NS5B polymerase, and an inhibitor of HCV helicase.

In some embodiments, the viral infection is an infection of the liver.

In some embodiments, the viral infection is HCV.

In some embodiments, the subject is mammalian.

In some embodiments, the subject is human.

Some embodiments of the compounds, compositions and methods provided herein include a method of inhibiting viral replication in a cell comprising contacting the cell with the compound of anyone of claims 1-12.

In some embodiments, the viral replication is RNA-dependent.

In some embodiments, the viral replication is HCV replication.

Some embodiments also include contacting the cell with a second or multiple antiviral agents.

In some embodiments, second or multiple antiviral agents are selected from the group consisting of ribavirin, levovirin, viramidine, thymosin alpha-1, interferon-λ, an inhibitor of HCV protease, an inhibitor of HCV NS5A replication complex, an inhibitor of HCV NS5B polymerase, a cyclophilin inhibitor, an inhibitor of inosine monophosphate dehydrogenase, interferon-α, and pegylated interferon-α.

In some embodiments, the second antiviral agent is interferon-α or pegylated interferon-α, alone or in combination with other antiviral agents.

In some embodiments, the cell is in vivo.

In some embodiments, the cell is ex vivo.

In some embodiments, the cell is a hepatocyte.

In some embodiments, the cell is mammalian.

In some embodiments, the cell is human.

Some embodiments of the compounds, compositions and methods provided herein include use of a compound provided herein in the treatment of a viral infection.

Some embodiments include the use of a compound provided herein in combination with a second therapeutic agent for the treatment of a viral infection.

In some embodiments, the second or multiple therapeutic agents are selected from the group consisting of thymosin alpha-1, interferon-λ, an inhibitor of HCV protease, an inhibitor of HCV NS5A replication complex, an inhibitor of HCV NS5B polymerase, an inhibitor of HCV helicase, a cyclophilin inhibitor, an inhibitor of inosine monophosphate dehydrogenase, interferon-α, and pegylated interferon-α.

In some embodiments, the second therapeutic agent is interferon-α or pegylated interferon-α, alone or in combination with other direct acting antivirals.

In some embodiments, the second therapeutic agent is a direct acting antiviral agent.

In some embodiments, the direct acting antiviral agent is selected from the group consisting of an inhibitor of HCV protease, an inhibitor of HCV NS5A replication complex, an inhibitor of HCV NS5B polymerase, and an inhibitor of HCV helicase.

In some embodiments, the viral infection is an infection of the liver.

In some embodiments, the viral infection is HCV.

In some embodiments, the subject is mammalian.

In some embodiments, the subject is human.

DETAILED DESCRIPTION

Some embodiments of the present invention relate to compounds, stereoisomers, pharmaceutically acceptable salts or prodrugs thereof or pharmaceutically acceptable salts useful to treat viral infections. In some embodiments, such compounds and compositions include Formula I:

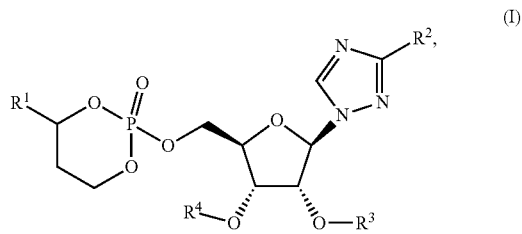

or a pharmaceutically acceptable salt thereof, wherein:

$R^1$ is an optionally substituted phenyl or an optionally substituted pyridyl;

$R^2$ is

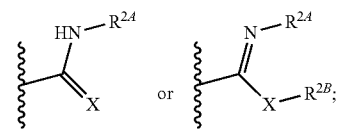

$R^{2A}$ is selected from the group consisting of H (hydrogen), a $C_1$-$C_6$ alkyl, a $C_1$-$C_6$ heteroalkyl, and a $C_1$-$C_6$ acyl;

$R^{2B}$ is selected from the group consisting of H (hydrogen), a $C_1$-$C_6$ alkyl, a $C_1$-$C_6$ heteroalkyl, and a $C_1$-$C_6$ acyl;

$R^3$ and $R^4$ are each independently selected from the group consisting of H (hydrogen), acyl, and heteroacyl; or $R^3$ and $R^4$ can be optionally linked to form a carbonyl; and X is O (oxygen), S (sulfur) or NH.

In some embodiments, $R^1$ is selected from the group consisting of:

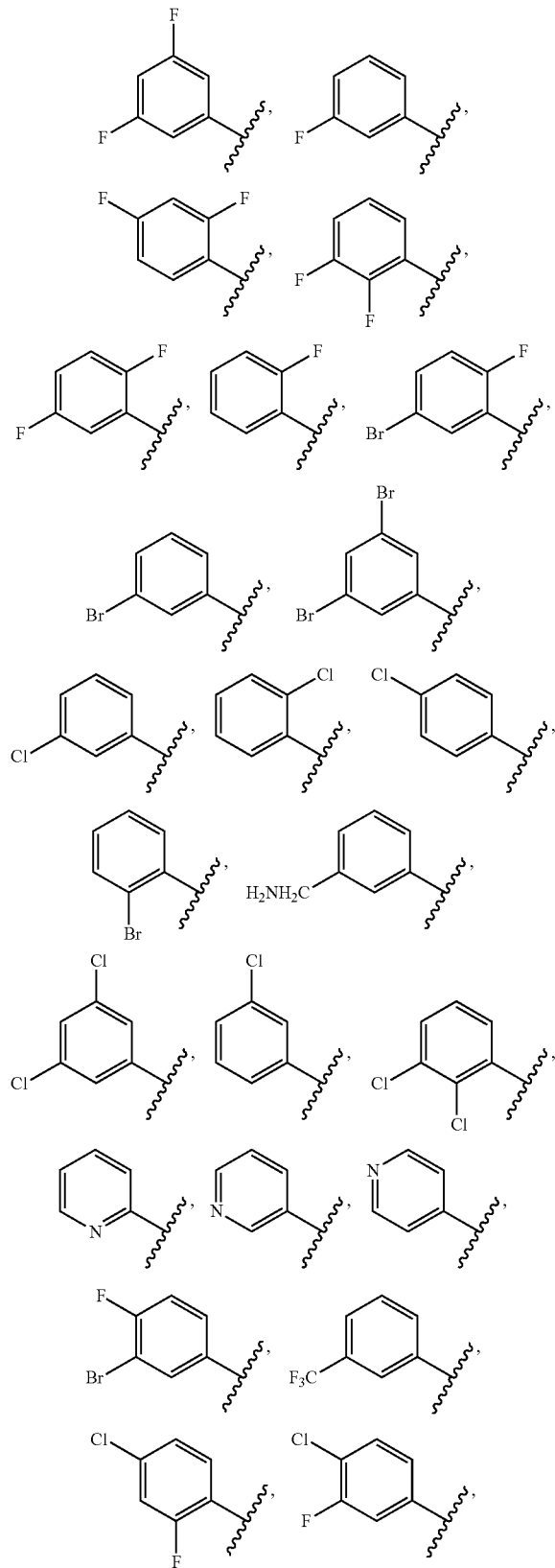

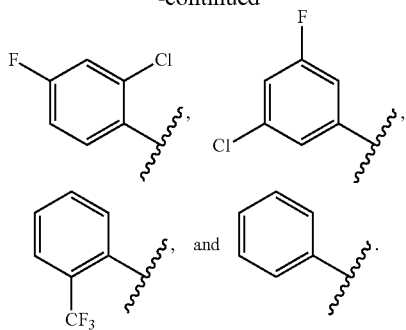

In some embodiments, $R^2$ is

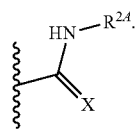

In some embodiments, X is O (oxygen).
In some embodiments, $R^{2A}$ is selected from the group consisting of H (hydrogen) and $C_1$-$C_6$ alkyl.
In some embodiments, $R^3$ and $R^4$ are each H, or $R^3$ and $R^4$ can be optionally linked to form a carbonyl.
In some embodiments, $R^2$ is

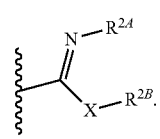

In some embodiments, X is O (oxygen).
In some embodiments, $R^{2A}$ is of H (hydrogen).
In some embodiments, $R^{2B}$ is $C_1$-$C_6$ alkyl.
In some embodiments, $R^3$ and $R^4$ are each independently selected from the group consisting of H (hydrogen), acyl, and heteroacyl.
In some embodiments, the compound is selected from the group consisting of 2R-(3-Aminocarbonyl-1H-1,2,4-triazole)-5R-(4S-(4-pyridinyl)-2-oxo-1,3,2-dioxaphosphorinanyloxymethyl)-3R,4R-dihydroxytetrahydrofuran, 2R-(3-Aminocarbonyl-1H-1,2,4-triazole)-5R-(4R-(4-pyridinyl)-2-oxo-1,3,2-dioxaphosphorinanyloxymethyl)-3R,4R-dihydroxytetrahydrofuran, 2R-(3-Aminocarbonyl-1H-1,2,4-triazole)-5R-(4S-(3-chlorophenyl)-2-oxo-1,3,2-dioxaphosphorinanyloxymethyl)-3R,4R-dihydroxytetrahydrofuran, 2R-(3-Aminocarbonyl-1H-1,2,4-triazole)-5R-(4R-(3-chlorophenyl)-2-oxo-1,3,2-dioxaphosphorinanyloxymethyl)-3R,4R-dihydroxytetrahydrofuran, 2R-(3-Aminocarbonyl-1H-1,2,4-triazole)-5R-(4S-(3-chlorophenyl)-2-oxo-1,3,2-dioxaphosphorinan-2R-yloxymethyl)-3R,4R-dihydroxytetrahydrofuran, 2R-(3-Aminocarbonyl-1H-1,2,4-triazole)-4R-(4S-(3-chlorophenyl)-2-oxo-1,3,2-dioxaphosphorinan-2R-yloxymethyl)-7-oxo-3,6,8-trioxa-cis-bicyclo[3.3.0]octane, 2R-(3-Aminocarbonyl-1H-1,2,4-triazole)-5R-(4S-(3-chlorophenyl)-2-oxo-1,3,2-dioxaphosphorinan-2R-yloxymethyl)-3R,4R-diacetyloxytetrahydrofuran, 2R-(3-(1-Ethoxy-1-iminomethyl)-1H-1,2,4-triazole)-5R-(4S-(3-chlorophenyl)-

2-oxo-1,3,2-dioxaphosphorinan-2R-yloxymethyl)-3R,4R-diacetyloxytetrahydrofuran, and 2R-(3-Ethylaminocarbonyl-1H-1,2,4-triazole)-5R-(4S-(3-chlorophenyl)-2-oxo-1,3,2-dioxaphosphorinan-2R-yloxymethyl)-3R,4R-diacetyloxytetrahydrofuran.

Compounds of Formula I have asymmetric centers where the stereochemistry is unspecified, and the stereoisomeric mixtures of these compounds are included, as well as the individual stereoisomers when referring to a compound of Formula I generally.

Some embodiments of the compounds, compositions and methods provided herein include a pharmaceutical composition comprising a compound provided herein and a pharmaceutically acceptable carrier.

Some embodiments of the compounds, compositions and methods provided herein include a method of treating a viral infection comprising administering an effective amount of a compound provided herein to a subject in need thereof.

Some embodiments also include administering an effective amount of a second or multiple therapeutic agents in combination with a compound provided herein to the subject in need thereof.

In some embodiments, the second or multiple therapeutic agents are selected from the group consisting of thymosin alpha-1, interferon-λ, an inhibitor of HCV protease, an inhibitor of HCV NS5A replication complex, an inhibitor of HCV NS5B polymerase, an inhibitor of HCV helicase, a cyclophilin inhibitor, an inhibitor of inosine monophosphate dehydrogenase, interferon-α, and pegylated interferon-α.

In some embodiments, the second therapeutic agent is interferon-α or pegylated interferon-α, alone or in combination with other direct acting antivirals.

In some embodiments, the second therapeutic agent is a direct acting antiviral agent.

In some embodiments, the direct acting antiviral agent is selected from the group consisting of an inhibitor of HCV protease, an inhibitor of HCV NS5A replication complex, an inhibitor of HCV NS5B polymerase, and an inhibitor of HCV helicase.

In some embodiments, the viral infection is an infection of the liver.

In some embodiments, the viral infection is HCV.
In some embodiments, the subject is mammalian.
In some embodiments, the subject is human.

Some embodiments of the compounds, compositions and methods provided herein include a method of inhibiting viral replication in a cell comprising contacting the cell with the compound of anyone of claims 1-12.

In some embodiments, the viral replication is RNA-dependent.

In some embodiments, the viral replication is HCV replication.

Some embodiments also include contacting the cell with a second or multiple antiviral agents.

In some embodiments, second or multiple antiviral agents are selected from the group consisting of thymosin alpha-1, interferon-λ, an inhibitor of HCV protease, an inhibitor of HCV NS5A replication complex, an inhibitor of HCV NS5B polymerase, an inhibitor of HCV helicase, a cyclophilin inhibitor, an inhibitor of inosine monophosphate dehydrogenase, interferon-α, and pegylated interferon-α.

In some embodiments, the second antiviral agent is interferon-α or pegylated interferon-α, alone or in combination with other direct acting antivirals.

In some embodiments, the second antiviral agent is a direct acting antiviral agent.

In some embodiments, the direct acting antiviral agent is selected from the group consisting of an inhibitor of HCV protease, an inhibitor of HCV NS5A replication complex, an inhibitor of HCV NS5B polymerase, an inhibitor of HCV helicase, and a cyclophilin inhibitor.

In some embodiments, the cell is in vivo.
In some embodiments, the cell is ex vivo.
In some embodiments, the cell is a hepatocyte.
In some embodiments, the cell is mammalian.
In some embodiments, the cell is human.

Some embodiments of the compounds, compositions and methods provided herein include use of a compound provided herein in the treatment of a viral infection.

In some embodiments, the compounds of the present invention can be used for inhibiting viral replication. In another aspect, the compounds of this invention can be used for inhibiting RNA-dependent RNA viral replication. In a further aspect, the compounds of this invention can be used for inhibiting HCV replication.

In another aspect, the compounds of the present invention can be used for treating viral infections of the liver. In a further aspect, compounds of this invention can be used for treating RNA-dependent RNA viral infection in the liver. In another aspect, compounds of this invention can be used for treating HCV infection in the liver.

In one aspect, inhibition of viral replication is measured in serum. Increased viral titer reduction is associated with decreased generation of viral mutants which are associated with drug resistance.

In another aspect, the compounds of the present invention can be used for preventing the onset of symptoms associated with a liver viral infection.

Activation of prodrugs of this invention results in the production of a nucleoside monophosphate (NMP). NMPs are frequently further phosphorylated inside the hepatocyte to the nucleoside diphosphate (NDP) and triphosphate (NTP). Drug elimination from the hepatocyte typically entails degradation of phosphorylated metabolites back to a species capable of being transported out of the hepatocyte and into the blood for elimination by the kidney or into the bile for biliary excretion. Often with nucleoside-based drug the phosphorylated metabolites are dephosphorylated to the uncharged nucleoside.

Nucleosides that leak back into the systemic circulation result in systemic exposure. If the nucleoside is active systemically, e.g. through entry into virally infected cells and phosphorylation to the active species, escape of the nucleoside from the liver leads to biological activity outside of the liver (i.e. extrahepatic tissues, blood cells). In this case, prodrugs of the invention can be effective for treating diseases outside of the liver, e.g. viral infections. Since many nucleosides exhibit poor oral bioavailability due to breakdown in the gastrointestinal tract either enzymatically (e.g. deamination by adenosine deaminase) or chemically (e.g. acid instability), the prodrug can be used for oral drug delivery. For nucleosides that are orally available via transporter-assisted absorption, the prodrug can be more effective in patients who have transporter deficiency. Moreover, given that the prodrugs in some cases are broken down or absorped slowly relative to the parent nucleoside, the prodrugs could advantageously result in increased active nucleotide exposure in the liver.

In other cases, however, systemic exposure to the nucleoside can result in toxicity. This can be minimized by selecting nucleosides that are preferentially excreted through the bile or nucleosides that are unable to undergo phosphorylation in tissues or nucleosides that undergo rapid intrahepatic metabolism to a biologically inactive metabolite. Some enzymes in the hepatocyte are present that can degrade nucleosides and therefore minimize exposure (e.g. Phase I and Phase II enzymes). One example is adenosine deaminase, which can deaminate some adenosine-based nucleosides to produce the corresponding inosine analogue. Rapid intracellular deamination of the nucleoside following its dephosphorylation to the nucleoside limits systemic exposure to the nucleoside and diminishes the risk of toxicity.

DEFINITIONS

In accordance with the present invention and as used herein, the following terms are defined with the following meanings, unless explicitly stated otherwise.

The term "alkyl" refers to saturated aliphatic groups including straight-chain, branched chain and cyclic groups, up to and including 10 carbon atoms. Suitable alkyl groups include methyl, ethyl, n-propyl, isopropyl, and cyclopropyl. The alkyl may be optionally substituted with 1-3 substituents.

The term "optionally substituted" or "substituted" includes groups substituted by one to four substituents, independently selected from lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halogen, lower alkylthio, oxo, lower acylalkyl, lower carboxy esters, carboxyl, -carboxamido, nitro, lower acyloxy, lower aminoalkyl, lower alkylaminoaryl, lower alkylaryl, lower alkylaminoalkyl, lower alkoxyaryl, lower arylamino, lower aralkylamino, lower alkylsulfonyl, lower-carboxamidoalkylaryl, lower-carboxamidoaryl, lower hydroxyalkyl, lower haloalkyl, lower alkylaminoalkylcarboxy-, lower aminocarboxamidoalkyl-, cyano, lower alkoxyalkyl, lower perhaloalkyl, and lower aralkyloxyalkyl. "Substituted aryl" and "substituted heteroaryl" refers to aryl and heteroaryl groups substituted with 1-6 substituents. These substituents are selected from the group consisting of lower alkyl, lower alkoxy, lower perhaloalkyl, halogen, hydroxy, cyano, and amino.

The term "heteroalkyl" refer to alkyl groups containing at least one heteroatom, in a further aspect are 1 to 3 heteroatoms. Suitable heteroatoms include oxygen, sulfur, and nitrogen.

The term "acyl" refers to —C(O)R where R is alkyl, or heteroalkyl.

The term "heteroacyl" refers to —C(O)R where R is heteroalkyl.

The term "carbonyl" refers to —C(O)—.

The term "alkenyl" refers to unsaturated groups which have 2 to 12 atoms and contain at least one carbon-carbon double bond and includes straight-chain, branched-chain and cyclic groups. Alkenyl groups may be optionally substituted. Suitable alkenyl groups include allyl. "1-Alkenyl" refers to alkenyl groups where the double bond is between the first and second carbon atom. If the 1-alkenyl group is attached to another group, e.g. it is a W substituent attached to the cyclic phosphate, it is attached at the first carbon.

The phrase "therapeutically effective amount" means an amount of a compound or a combination of compounds that ameliorates, attenuates or eliminates one or more of the symptoms of a particular disease or condition or prevents, modifies, or delays the onset of one or more of the symptoms of a particular disease or condition.

The term "pharmaceutically acceptable salt" includes salts of compounds of Formula I and its prodrugs derived from the combination of a compound of this invention and an organic or inorganic acid or base. Suitable acids include acetic acid, adipic acid, benzenesulfonic acid, (+)-7,7-dimethyl-2-oxobicyclo[2.2.1]heptane-1-methanesulfonic acid, citric acid, 1,2-ethanedisulfonic acid, dodecyl sulfonic acid, fumaric acid, glucoheptonic acid, gluconic acid, glucuronic acid, hippuric acid, hydrochloride hemiethanolic acid, HBr, HCl, HI, 2-hydroxyethanesulfonic acid, lactic acid, lactobionic acid, maleic acid, methanesulfonic acid, methylbromide acid, methyl sulfuric acid, 2-naphthalenesulfonic acid, nitric acid, oleic acid, 4,4'-methylenebis[3-hydroxy-2-naphthalenecarboxylic acid], phosphoric acid, polygalacturonic acid, stearic acid, succinic acid, sulfuric acid, sulfosalicylic acid, tannic acid, tartaric acid, terephthalic acid, and p-toluenesulfonic acid.

The term "patient" refers to an animal being treated including a mammal, such as a dog, a cat, a cow, a horse, a sheep, and a human. Another aspect includes a mammal, both male and female.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g. HO—, HS—, HOOC—, $R_2N$—, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of Formula I fall within this scope. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Prodrugs are described in The Organic Chemistry of Drug Design and Drug Action, by Richard B. Silverman, Academic Press, San Diego, 1992. Chapter 8: "Prodrugs and Drug delivery Systems" pp. 352-401; Design of Prodrugs, edited by H. Bundgaard, Elsevier Science, Amsterdam, 1985; Design of Biopharmaceutical Properties through Prodrugs and Analogs, Ed. by E. B. Roche, American Pharmaceutical Association, Washington, 1977; and Drug Delivery Systems, ed. by R. L. Juliano, Oxford Univ. Press, Oxford, 1980.

The term "cyclic phosphate ester of 1,3-propanediol", "cyclic phosphate diester of 1,3-propanediol", "2 oxo $2\lambda^5$ [1,3,2]dioxaphosphorinane", "2-oxo-[1,3,2]-dioxaphosphorinane", or "dioxaphosphorinane" refers to the following:

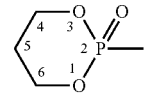

The term "cis" stereochemistry refers to the spatial relationship of the R group and the substituent attached to the phosphorus atom via an exocyclic single bond on the six membered 2-oxo-phosphorinane ring. The structures A and B below show two possible cis-isomers of 2- and 4-substituted 2-oxo-phosphorinane. Structure A shows cis-isomer of (2S, 4R)-configuration whereas structure B shows cis-isomer of (2R,4S)-configuration.

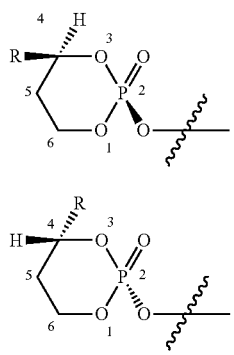

The term "trans" stereochemistry refers to the spatial relationship of the R group and the substituent attached to the phosphorus atom via an exocyclic single bond on the six membered 2-oxo-phosphorinane ring. The structures C and D below show two possible trans-isomers of 2- and 4-substituted 2-oxo-phosphorinane. Structure C shows trans-isomer of (2S,4S)-configuration whereas structure D shows trans-isomer of (2R,4R)-configuration.

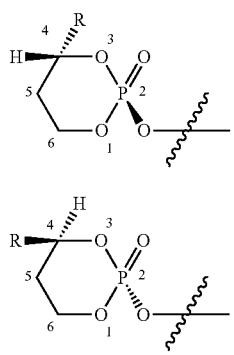

The term "percent enantiomeric excess (% ee)" refers to optical purity. It is obtained by using the following formula:

$$\frac{[R]-[S]}{[R]+[S]} \times 100 = \%R - \%S$$

where [R] is the amount of the R isomer and [S] is the amount of the S isomer. This formula provides the % ee when R is the dominant isomer.

The term "enantioenriched" or "enantiomerically enriched" refers to a sample of a chiral compound that consists of more of one enantiomer than the other. The extent to which a sample is enantiomerically enriched is quantitated by the enantiomeric ratio or the enantiomeric excess.

The term "liver" refers to liver organ.

The term "enhancing" refers to increasing or improving a specific property.

The term "liver specificity" refers to the ratio:

$$\frac{[\text{drug or a drug metabolite in liver tissue}]}{[\text{drug or a drug metabolite in blood or another tissue}]}$$

as measured in animals treated with the drug or a prodrug. The ratio can be determined by measuring tissue levels at a specific time or may represent an AUC based on values measured at three or more time points.

The term "increased or enhanced liver specificity" refers to an increase in the liver specificity ratio in animals treated with the prodrug relative to animals treated with the parent drug.

The term "enhanced oral bioavailability" refers to an increase of at least 50% of the absorption of the dose of the parent drug. In an additional aspect the increase in oral bioavailability of the prodrug (compared to the parent drug) is at least 100%, that is a doubling of the absorption. Measurement of oral bioavailability usually refers to measurements of the prodrug, drug, or drug metabolite in blood, plasma, tissues, or urine following oral administration compared to measurements following parenteral administration.

The term "therapeutic index" refers to the ratio of the dose of a drug or prodrug that produces a therapeutically beneficial response relative to the dose that produces an undesired response such as death, an elevation of markers that are indicative of toxicity, and/or pharmacological side effects.

The term "sustained delivery" refers to an increase in the period in which there is a prolongation of therapeutically-effective drug levels due to the presence of the prodrug.

The term "bypassing drug resistance" refers to the loss or partial loss of therapeutic effectiveness of a drug (drug resistance) due to changes in the biochemical pathways and cellular activities important for producing and maintaining the biological activity of the drug and the ability of an agent to bypass this resistance through the use of alternative pathways or the failure of the agent to induce changes that tend to resistance.

The terms "treating" or "treatment" of a disease includes inhibiting the disease (slowing or arresting its development), providing relief from the symptoms or side-effects of the disease (including palliative treatment), and relieving the disease (causing regression of the disease).

Methods described in Examples A-D were used to test activation of compounds of this invention. Methods used in Example E were used to evaluate the ability of compounds of the invention to generate NTPs.

HCV replication in human liver tissue was evaluated as in Example F. Liver specificity of the prodrugs relative to the nucleosides was measured by methods in Example G.

Tissue distribution can be determined according to methods in Example H. Oral bioavailability was determined by methods described in Example I.

In one aspect of the present invention, the RNA-dependent RNA viral infection is a positive-sense single-stranded RNA-dependent viral infection. In another aspect, the positive-sense single-stranded RNA-dependent RNA viral infection is Flaviviridae viral infection or Picornaviridae viral infection. In a subclass of this class, the Picornaviridae viral infection is rhinovirus infection, poliovirus infection, or hepatitis A virus infection. In a second subclass of this class, the Flaviviridae viral infection is selected from the group consisting of hepatitis C virus infection, yellow fever virus infection, dengue virus infection, West Nile virus infection, Japanese encephalitis virus infection, Banzi virus infection, and bovine viral diarrhea virus infection. In a subclass of this subclass, the Flaviviridae viral infections hepatitis C virus infection.

In a further aspect, compounds of the present invention can be used to enhance the oral bioavailability of the parent drug. In another aspect, compounds of the present invention can be used to enhance the oral bioavailability of the parent drug by at least 5%. In another aspect, compounds of the present invention can be used to enhance the oral bioavailability of the parent drug by at least 10%. In another aspect, oral bioavailability is enhanced by 50% compared to the parent drug administered orally. In a further aspect, the oral bioavailability is enhanced by at least 100%.

In another aspect, compounds of the present invention can be used to increase the therapeutic index of a drug.

In one aspect, compounds of the present invention can be used to bypass drug resistance.

In another aspect, compounds of the present invention can be used to treat a special group of patients who are poor responders to ribavirin due to transporter deficiency.

Formulations

Compounds of the invention are administered in a total daily dose of 0.01 to 1000 mg/kg. In one aspect the range is about 0.1 mg/kg to about 100 mg/kg. In another aspect the range is 0.5 to 20 mg/kg. The dose may be administered in as many divided doses as is convenient.

Compounds of this invention when used in combination with other antiviral agents may be administered as a daily dose or an appropriate fraction of the daily dose (e.g., bid). Administration of the prodrug may occur at or near the time in which the other antiviral is administered or at a different time. The compounds of this invention may be used in a multidrug regimen, also known as combination or 'cocktail' therapy, wherein, multiple agents may be administered together, may be administered separately at the same time or at different intervals, or administered sequentially. The compounds of this invention may be administered after a course of treatment by another agent, during a course of therapy with another agent, administered as part of a therapeutic regimen, or may be administered prior to therapy by another agent in a treatment program.

Pharmaceutically acceptable salts include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, palmoate, phosphate, polygalacturonate, stearate, succinate, sulfate, sulfosalicylate, tannate, tartrate, teraphthalate, tosylate, and triethiodide.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, ethylcellulose, hydroxypropylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachid oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachid oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The amount of active ingredient that may be combined with the carrier material to produce a single dosage form will vary depending upon the host treated and the particular mode of administration. For example, a time-release formulation intended for oral administration to humans may contain 20 to 2000 µmol (approximately 10 to 1000 mg) of active material compounded with an appropriate and convenient amount of carrier material which may vary from about 5 to about 95% of the total compositions. It is preferred that the pharmaceutical composition be prepared which provides easily measurable amounts for administration. For example, an aqueous solution intended for intravenous infusion should contain from about 0.05 to about 50 µmol (approximately 0.025 to 25 mg) of the active ingredient per milliliter of solution in order that infusion of a suitable volume at a rate of about 30 mL/h can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of Formula I when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Formulations suitable for parenteral administration may be administered in a continuous infusion manner via an indwelling pump or via a hospital bag. Continuous infusion includes the infusion by an external pump. The infusions may be done through a Hickman or PICC or any other suitable means of administering a formulation either parenterally or i.v.

Preferred unit dosage formulations are those containing a daily dose or unit, daily sub-dose, or an appropriate fraction thereof, of a drug. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Some embodiments are concerned with a method of inhibiting HCV replication or treating HCV infection with a compound provided herein in combination with one or more agents useful for treating HCV infection. Such agents active against HCV include, but are not limited to, thymosin alpha-1, interferon-β, interferon-α, interferon-λ, pegylated interferon-α (peginterferon-α), Interferon-α includes, but is not limited to, recombinant interferon-α2a (such as Roferon interferon available from Hoffmann-LaRoche, Nutley, N.J.), pegylated interferon-α2a (Pegasys™), interferon-α2b (such as Intron-A interferon available from Schering Corp., Kenilworth, N.J.), pegylated interferon-α2b (PegIntron™), a recombinant consensus interferon (such as interferon alpha-con-1), and a purified interferon-α product. Amgen's recombinant consensus interferon has the brand name Infergen®. Some embodiments are therefore to be understood as embracing all such regimes of simultaneous or alternating treatment, and the term "administering" is to be interpreted accordingly. It will be understood that the scope of combinations of the compounds provided herein with other agents useful for treating HCV infection includes in principle any combination with any pharmaceutical composition for treating HCV infection. When a compound provided herein or a pharmaceutically acceptable salt thereof is used in combination with a second therapeutic agent active against HCV, the dose of each compound may be either the same as or different from the dose when the compound is used alone.

Some embodiments include a pharmaceutical composition comprising a compound of Formula I or pharmaceutically acceptable salt thereof and at least one agent useful for treating a viral infection, particularly an HCV infection.

For the treatment of HCV infection, the compounds provided herein may also be administered in combination with an agent that is an inhibitor of HCV protease. HCV protease is an essential viral enzyme and has been demonstrated to be an excellent target for inhibition of HCV replication. Specific embodiments of HCV protease inhibitors for combination with the compounds provided herein are telaprevir, boceprevir, faldaprevir, simeprevir, vaniprevir, asunaprevir, danoprevir, ACH-1625, ACH-2684, ABT-450, GS-9256, GS-9451, MK-5172, and IDX320.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds provided herein may also be administered in combination with an inhibitor of IMPDH, such as VX-497 (merimepodib), which is disclosed in WO 97/41211 and WO 01/00622 (assigned to Vertex); another IMPDH inhibitor, such as that disclosed in WO 00/25780 (assigned to Bristol-Myers Squibb); or mycophenolate mofetil [see A. C. Allison and E. M. Eugui, Agents Action, 44 (Suppl.): 165 (1993)].

The compounds provided herein may also be combined for the treatment of HCV infection with nucleoside-based inhibitors of HCV NS5B polymerase. Such inhibitors include, but are not limited to, GS-7977, mericitabine, GS-6620, IDX184, IDX368, ALS-2200, ALS-2158, BCX5191, and EP-NI266.

The compounds provided herein may also be combined for the treatment of HCV infection with non-nucleoside inhibitors of HCV polymerase. Such inhibitors include, but are not limited to, setrobuvir, ABT-333, ABT-072, BI207127, filibuvir, BMS-791325, tegobuvir, VX-222, GS-9669, TMC647055, PPI-383, and VLS-732.

The compounds provided herein may also be combined for the treatment of HCV infection with inhibitors of HCV NS5A replication complex. Such inhibitors include, but are not limited to, daclatasvir, GS-5885, ABT-267, RO5466731, GSK2336805, IDX719, ACH-2928, ACH-3102, JNJ-47910382, MK-8742, PPI-668, PPI-461, and BMS-824393.

The compounds provided herein may also be combined for the treatment of HCV infection with cyclophilin inhibitors. Such inhibitors include, but are not limited to, alisporivir, NIM811, and BC556.

The compounds provided herein may also be combined for the treatment of HCV infection with other types of inhibitors. Such inhibitors include, but are not limited to, BMS-914143, miravirsen, BMS-929075, MK-6325, MK-2748, MK-8325, ITX 5061, BL-8020, infradure, and TG4040.

Synthesis of Compounds

General synthesis of the compounds of liver-targeting nucleoside prodrug derivatives has been discussed in detail previously (U.S. Pat. No. 7,666,855, incorporated herein by reference in its entirety). Scheme I describes general strategies of synthesis of the 5'-nucleoside monophosphate prodrug analogs. The first strategy starts with protection of the 2',3'-hydroxy groups of nucleosides of structure 1 to generate intermediates of structure 2. The phosphate group is introduced by reaction of compounds of structure 2 and a reagent of structure 3 to give the monophosphate compounds of structure 4 following a deprotection of the hydroxy protection groups. Treatment of compounds of structure 4 with an acylating reagent of structure 5 provides the final compounds of structure 6. Alternatively, nucleoside of structure 1 can be phosphorylated directly with reagent of structure 3 without protection of the 2',3'-dihydroxy and then be acylated to afford the final compounds of structure 6. The third strategy is to prepare the intermediates of structure 7 and then is converted to final compounds of structure 6 by treatment with reagent of structure 3.

Scheme I

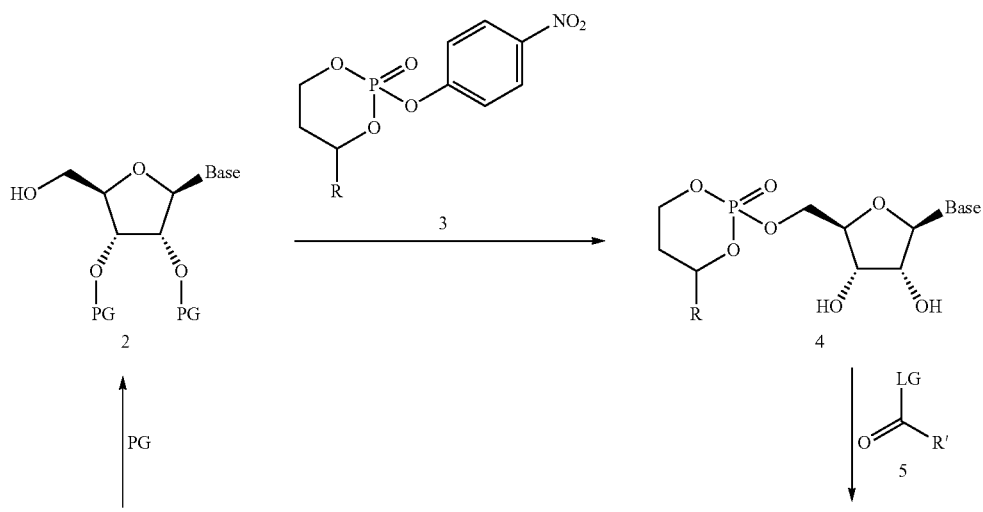

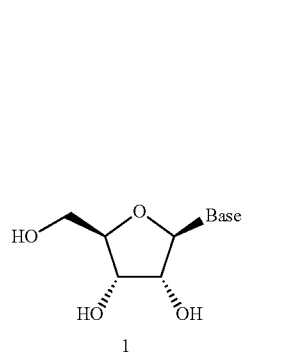
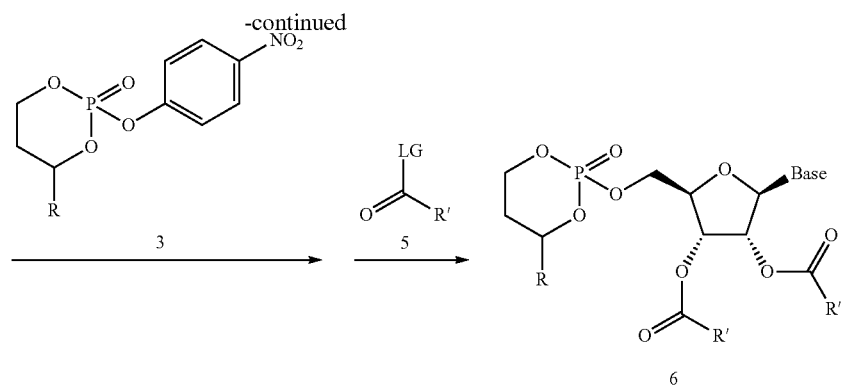
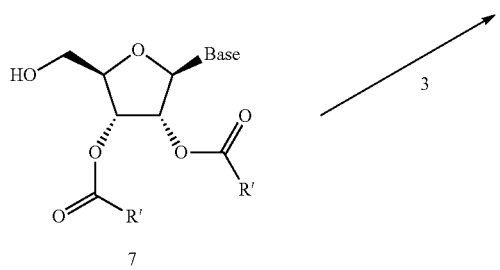

EXAMPLES

Some compounds of Formula I can be prepared as outlined below.

Example 1

2R-(3-Aminocarbonyl-1H-1,2,4-triazole)-5R-(4S-(4-pyridinyl)-2-oxo-1,3,2-dioxaphosphorinanyloxymethyl)-3R,4R-dihydroxytetrahydrofuran (Compound 101) and 2R-(3-Aminocarbonyl-1H-1,2,4-triazole)-5R-(4R-(4-pyridinyl)-2-oxo-1,3,2-dioxaphosphorinanyloxymethyl)-3R,4R-dihydroxytetrahydrofuran (Compound 102)

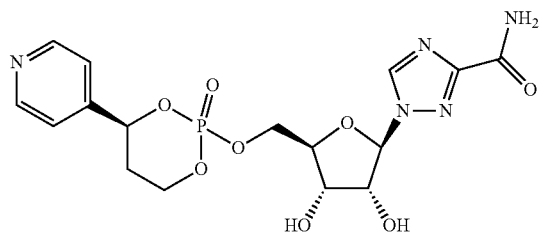

(101)

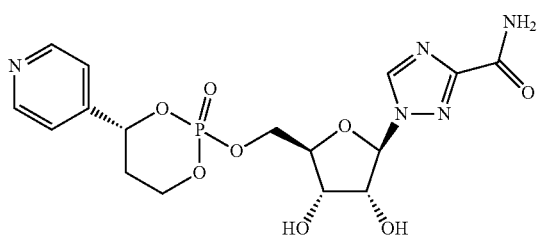

(102)

Compounds 101 and 102 were prepared according synthetic strategy of Scheme I from 1-(((2R,3R,4S,5R)-3,4-dihydroxy-5-(hydroxymethyl)oxolan-2-yl)-1H-1,2,4-triazole-3-carboxamide (ribavirin).

To a solution of ribavirin (0.12 g, 0.5 mmol) and (±)-2-(N,N-diisopropylamine)-4-(4-pyridinyl)-1,3-dioxaphosphorinane (0.16 g, 0.6 mmol) in DMF (5 mL) at room temperature was added benzimidazolium triflate (0.17 g, 0.6 mmol) and the reaction mixture was stirred for 30 minutes before cooling to −40° C. tert-Butylhydroperoxide (0.25 mL) was then added at the low temperature and the mixture was warmed to room temperature for 1 hour. Standard work up followed by chromatography afforded a diastereomeric mixture of compounds 101 and 102 (0.10 g, 45%); mp: 162-164° C., MH+: 442.

Example 2

2R-(3-Aminocarbonyl-1H-1,2,4-triazole)-5R-(4S-(3-chlorophenyl)-2-oxo-1,3,2-dioxaphosphorinanyloxymethyl)-3R,4R-dihydroxytetrahydrofuran (Compound 103) and 2R-(3-Aminocarbonyl-1H-1,2,4-triazole)-5R-(4R-(3-chlorophenyl)-2-oxo-1,3,2-dioxaphosphorinanyloxymethyl)-3R,4R-dihydroxytetrahydrofuran (Compound 104)

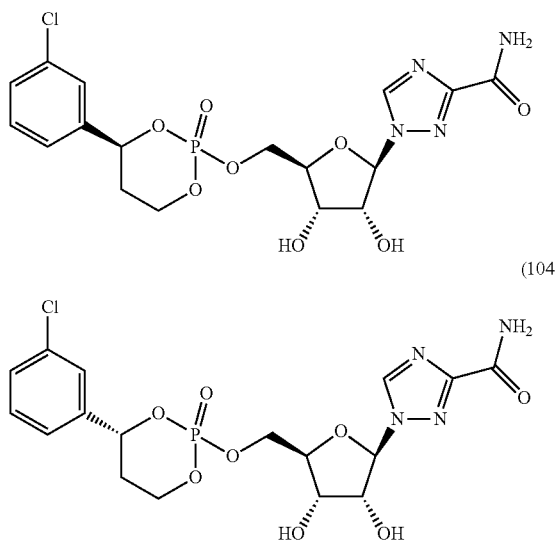

Compounds 103 and 104 were prepared as a diastereomeric mixture in a similar fashion as described in Example 1 from 1-((2R,3R,4S,5R)-3,4-dihydroxy-5-(hydroxymethyl)oxolan-2-yl)-1H-1,2,4-triazole-3-carboxamide and (±)-2-(N,N-diisopropylamine)-4-(3-chlorophenyl)-1,3-dioxaphosphorinane; mp: 101-102° C., MH+: 475.

Example 3

2R-(3-Aminocarbonyl-1H-1,2,4-triazole)-5R-(4S-(3-chlorophenyl)-2-oxo-1,3,2-dioxaphosphorinan-2R-yloxymethyl)-3R,4R-dihydroxytetrahydrofuran (Compound 105)

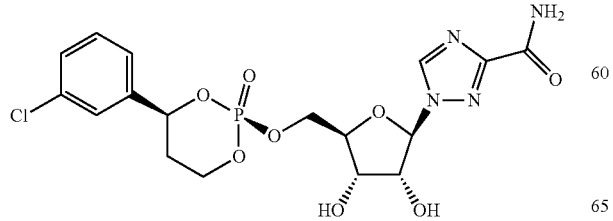

Compound 105 was prepared according synthetic strategy of Scheme I from 1-((2R,3R,4S,5R)-3,4-dihydroxy-5-(hydroxymethyl)oxolan-2-yl)-1H-1,2,4-triazole-3-carboxamide and (−)-4S-(3-chlorophenyl)-2-trans-(4-nitrophenoxy)-2-oxo-1,3,2-dioxaphosphorinane: $^1$H-NMR (400 MHz, DMSO) 8.82 (s, 1H), 7.85 (bs, 1H), 7.62 (bs, 1H), 7.46-7.40 (m, 3H), 7.38-7.33 (m, 1H), 5.93 (d, J=2.8, 1H), 5.73 (d, J=5.2, 1H), 5.71-5.66 (m, 1H), 5.44 (d, J=5.6, 1H), 4.55-4.15 (m, 8H), and 2.27-2.10 (m, 2H).

Example 4

2R-(3-Aminocarbonyl-1H-1,2,4-triazole)-4R-(4S-(3-chlorophenyl)-2-oxo-1,3,2-dioxaphosphorinan-2R-yloxymethyl)-7-oxo-3,6,8-trioxa-cis-bicyclo[3.3.0]octane (Compound 106)

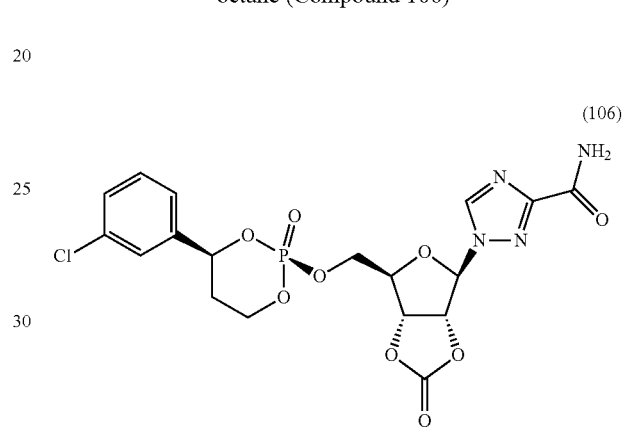

Compound 106 can be prepared according synthetic strategy of Scheme I from compound 105.

Example 5

2R-(3-Aminocarbonyl-1H-1,2,4-triazole)-5R-(4S-(3-chlorophenyl)-2-oxo-1,3,2-dioxaphosphorinan-2R-yloxymethyl)-3R,4R-diacetyloxytetrahydrofuran (Compound 107)

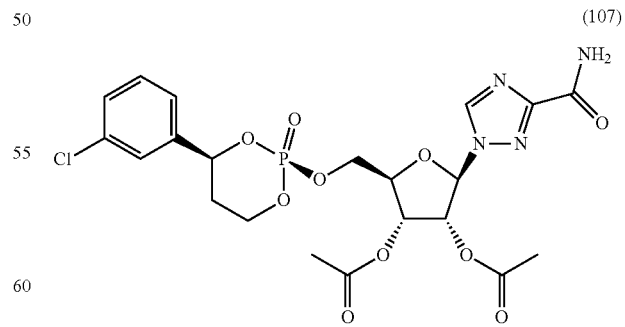

Compound 107 was prepared according synthetic strategy of Scheme I from compound 103: $^1$H-NMR (400 MHz, DMSO) 8.85 (s, 1H), 7.88 (bs, 1H), 7.68 (bs, 1H), 7.49-7.40 (m, 3H), 7.36-7.30 (m, 1H), 6.37 (d, J=3.2, 1H), 5.71-5.65 (m, 2H), 5.64 (t, J=6.2, 1H), 4.60-4.25 (m, 5H), 2.23-2.12 (m, 2H), 2.12 (s, 3H), and 2.19 (s, 3H).

Example 6

2R-(3-(1-Ethoxy-1-iminomethyl)-1H-1,2,4-triazole)-5R-(4S-(3-chlorophenyl)-2-oxo-1,3,2-dioxaphosphorinan-2R-yloxymethyl)-3R,4R-diacetyloxytetrahydrofuran (Compound 108)

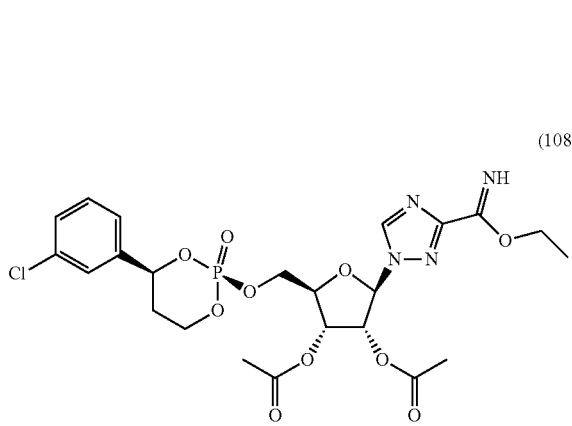

(108)

Compound 108 can be prepared according synthetic strategy of Scheme I from 1-((2R,3R,4S,5R)-3,4-dihydroxy-5-(hydroxymethyl)oxolan-2-yl)-1H-1,2,4-triazole-3-carboxamide.

Example 7

2R-(3-Ethylaminocarbonyl-1H-1,2,4-triazole)-5R-(4S-(3-chlorophenyl)-2-oxo-1,3,2-dioxaphosphorinan-2R-yloxymethyl)-3R,4R-diacetyloxytetrahydrofuran (Compound 109)

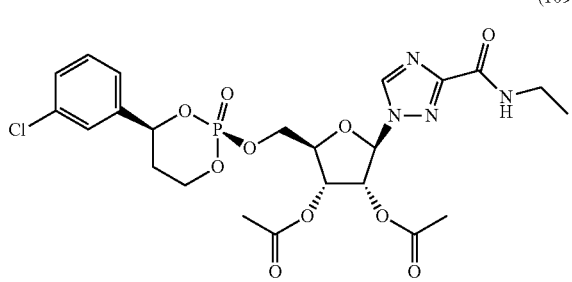

(109)

Compound 109 can be prepared according synthetic strategy of Scheme I from 1-((2R,3R,4S,5R)-3,4-dihydroxy-5-(hydroxymethyl)oxolan-2-yl)-1H-1,2,4-triazole-3-carboxamide.

Example 8

(2R,3R,4R,5R)-2-(3-Carbamoyl-1H-1,2,4-triazol-1-yl)-5-(((((2R,4S)-4-(3-chlorophenyl)-2-oxido-1,3,2-dioxaphosphinan-2-yl)oxy)methyl)tetrahydrofuran-3,4-diyl dipropionate (Compound 110)

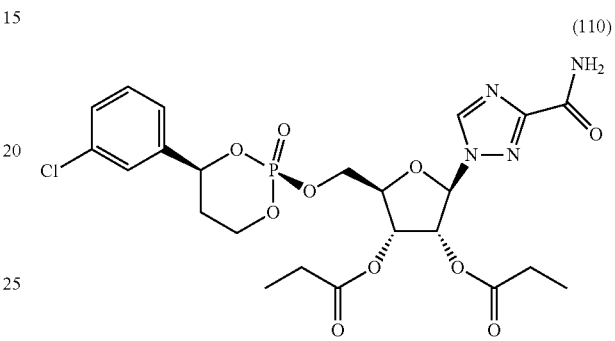

(110)

Compound 110 was prepared according synthetic strategy of Scheme I from compound 103: $^1$H-NMR (400 MHz, DMSO) 8.85 (s, 1H), 7.88 (bs, 1H), 7.68 (bs, 1H), 7.45-7.40 (m, 3H), 7.36-7.30 (m, 1H), 6.37 (d, J=2.8, 1H), 5.71-5.65 (m, 2H), 5.62 (t, J=5.6, 1H), 4.60-4.25 (m, 5H), 3.48-3.42 (m, 1H), 2.41-2.30 (m, 4H), 2.23-2.13 (m, 2H), and 1.07-1.00 (m, 7H).

Biological Examples

Examples of use of the method of the invention include the following. It will be understood that these examples are exemplary and that the method of the invention is not limited solely to these examples.

For the purposes of clarity and brevity, chemical compounds are referred to as synthetic example numbers in the biological examples below.

Example A

In Vitro Activation of Prodrug Analogues by Rat Liver Microsomes. Quantification by by-Product Capture

The prodrug analogues were tested for activation in rat liver microsomes by means of a prodrug byproduct capture assay.

Methods:

Prodrugs were tested for activation by liver microsomes isolated from rats induced with dexamethasone to enhance CYP3A4 activity (Human Biologics Inc., Phoenix Ariz.). The study was performed at 2 mg/mL rat liver microsomes, 100 mM $KH_2PO_4$, 10 mM glutathione, 25 μM or 250 μM compound, and 2 mM NADPH for 0-7.5 min. in an Eppendorf Thermomixer 5436 at 37° C., speed 6. The reactions were initiated by addition of NADPH following a 2-min. preincubation. Reactions were quenched with 60% methanol at 0, 2.5, 5, and 7.5 min L-Glutamyl-L-(S-(3-oxo-3-(3-chlorophenyl)propyl)cysteinylglycine, a glutathione adduct of the byproduct of prodrug activation, 3-chlorophenyl vinyl ketone, was quantified following extraction of the reaction with 1.5 volumes of methanol. The extracted samples were centrifuged at 14,000 rpm in an Eppendorf microfuge and the supernatant analyzed by HPLC for L-glutamyl-L-(S-(3-oxo-3-(3-chlorophenyl)propyl)cysteinylglycine content. Spiked L-glutamyl-L-(S-(3-oxo-3-(3-chlorophenyl)propyl)cysteinylglycine standards (1-30 μM) were prepared in 2 mg/mL microsomes under reaction conditions and then quenched and processed in an identical fashion to unknown samples. For HPLC analysis, the loading mobile phase buffer (Buffer A) consisted of a 9:1 ratio (v/v) of 20 mM potassium phosphate, pH 6.2 and acetonitrile. Extract (100 μL) was injected onto a Beckman Ultrasphere ODS column (4.6×250 mM). The column was eluted with a gradient to 60% acetonitrile. The elution of L-glutamyl-L-(S-(3-oxo-3-(3-chlorophenyl)propyl)cysteinylglycine (retention time 10.4 min.) was monitored at 245 nm.

Example B

In Vitro Activation of Prodrug Analogues by Rat Liver Microsomes. Quantification by LC-MS/MS Prodrug analogues were tested for activation to NMP in reactions catalyzed by the microsomal fraction of rat liver.
Methods:
Prodrugs were tested for activation by liver microsomes isolated from rats induced with dexamethasone to enhance CYP3A4 activity (Human Biologics Inc., Phoenix Ariz.). Reactions were conducted in 0.1 M $KH_2PO_4$, pH 7.4, in the presence of 2 mM NADPH and liver microsomes (1 mg/mL). Reaction mixtures were incubated for 5 min. in an Eppendorf Thermomixer 5436 (37° C., speed 6). Reactions were terminated by the addition of 1.5 volumes of methanol. The resulting extracts were clarified by centrifugation at 14,000 rpm in an Eppendorf microfuge (20 min) The supernatants (200 μL) were evaporated under vacuum and heat to dryness. The dried residue was reconstituted with 200 μL of water and the mixture was centrifuged for 10 min at 14,000 rpm. A mixture of 35 μL aliquot of supernatant and 35 μL of mobile phase A (20 mM N—N-dimethylhexylamine and 10 mM propionic acid in 20% methanol) was analyzed by LC-MS/MS (Applied Biosystems, API 4000) equipped with an Agilent 1100 binary pump and a LEAP injector. NMP was detected by using MS/MS mode ($M^-$/78.8) and quantified based on comparison to a standard of lamivudine monophosphate.

Example C

In Vitro Activation in Human Liver Microsomes, Quantification by by-Product Capture The prodrug analogues are tested for activation in human liver microsomes.
Methods:
Human liver microsomes are purchased from In Vitro Technologies (IVT1032). The study is performed at 2 mg/mL human liver microsomes, 100 mM $KH_2PO_4$, 10 mM glutathione, 25 μM or 250 μM compound, and 2 mM NADPH for 0-7.5 min. in an Eppendorf Thermomixer 5436 at 37° C., speed 6. The reactions are initiated by addition of NADPH following a 2-mM preincubation. Reactions are quenched with 60% methanol at 0, 2.5, 5, and 7.5 min. L-Glutamyl-L-(S-(3-oxo-3-(3-chlorophenyl)propyl)cysteinylglycine, a glutathione adduct of the by-product of prodrug activation, 3-chlorophenyl vinyl ketone, is quantified following extraction of the reaction with 1.5 volumes of methanol. The extracted samples are centrifuged at 14,000 rpm in an Eppendorf microfuge and the supernatant analyzed by HPLC for L-glutamyl-L-(S-(3-oxo-3-(3-chlorophenyl)propyl)cysteinylglycine content. Spiked L-glutamyl-L-(S-(3-oxo-3-(3-chlorophenyl)propyl)cysteinylglycine standards (1-30 μM) are prepared in 2 mg/mL microsomes under reaction conditions and then quenched and processed in an identical fashion to unknown samples. For HPLC analysis, the loading mobile phase buffer (Buffer A) consists of a 9:1 ratio (v/v) of 20 mM potassium phosphate, pH 6.2 and acetonitrile. Extract (100 μL) is injected onto a Beckman Ultrasphere ODS column (4.6×250 mM). The column is eluted with a gradient to 60% acetonitrile. The elution of L-glutamyl-L-(S-(3-oxo-3-(3-chlorophenyl)propyl)cysteinylglycine (retention time 10.4 min) is monitored at 245 nm.

Example D

In Vitro Activation of Prodrug Analogues by Human Liver Microsomes, Quantification by LC-MS/MS Prodrug analogues were tested for activation to NMP in reactions catalyzed by the microsomal fraction of human liver.
Methods:
Prodrugs were tested for activation by human liver microsomes purchased from In Vitro Technologies (IVT1032). Reactions were conducted in 0.1 M $KH_2PO_4$, pH 7.4, in the presence of 2 mM NADPH and liver microsomes (1 mg/mL). Reaction mixtures were incubated for 5 min. in an Eppendorf Thermomixer 5436 (37° C., speed 6). Reactions were terminated by the addition of 1.5 volumes of methanol. The resulting extracts were clarified by centrifugation at 14,000 rpm in an Eppendorf microfuge (20 min) The supernatants (200 μL) were evaporated under vacuum and heated to dryness. The dried residue was reconstituted with 200 μL of water and the mixture was centrifuged for 10 min at 14,000 rpm. A mixture of 35 μL aliquot of supernatant and 35 μL of mobile phase A (20 mM N—N-dimethylhexylamine and 10 mM propionic acid in 20% methanol) was analyzed by LC-MS/MS (Applied Biosystems, API 4000) equipped with an Agilent 1100 binary pump and a LEAP injector. NMP was detected by using MS/MS mode ($M^-$/78.8) and quantified based on comparison to a standard of lamivudine monophosphate.

Example E

NTP Accumulation in Hepatocytes Following Incubation with Nucleoside Analogues and their Prodrugs Nucleoside analogues and their prodrugs were evaluated for their ability to generate NTPs in freshly isolated rat hepatocytes. It is generally accepted that the NTP form of a nucleoside is the active antiviral agent.
Methods:
Hepatocytes were prepared from fed Sprague-Dawley rats (250-300 g) according to the procedure of Berry and Friend (Berry, M. N. Friend, D. S., *J. Cell Biol.* 43:506-520 (1969)) as modified by Groen (Groen, A. K. et al., *Eur. J. Biochem* 122:87-93 (1982)). Hepatocytes (20 mg/mL wet weight, >85% trypan blue viability) were incubated at 37° C. in 2 mL of Krebs-bicarbonate buffer containing 20 mM glucose, and 1 mg/mL BSA for 2 h in the presence of 1-250 μM nucleoside or prodrug (from 25 mM stock solutions in DMSO). Following the incubation, 1600 μL aliquot of the cell suspension was centrifuged and 300 μL of acetonitrile was added to the pellet, vortexed and sonicated until the pellet broke down. Then 200 μL of water was added to make a 60% acetonitrile solution. After 10 min centrifugation at 14,000 rpm, the resulting supernatant was transferred to a new vial and evaporated to near dryness in a Savant SpeedVac Plus at room temperature. The dried residue was reconstituted with 200 μL of water and the mixture was centrifuged for 10 min at 14,000 rpm. A mixture of 35 μL aliquot of supernatant and 35 μL of mobile phase A (20 mM N—N-dimethylhexylamine and 10 mM propionic acid in 20% methanol) was analyzed by LC-MS/MS (Applied Biosystems, API 4000) equipped with an Agilent 1100 binary pump and a LEAP injector. NTP was detected by using MS/MS mode (M$^-$/78.8) and quantified based on comparison to a standard of the nucleoside triphosphate.

Example F

HCV-Infected Human Liver Slice Assay

Inhibition of HCV replication in human liver tissue was evaluated using the following assay.
Methods:
Procurement: Liver from a brain-dead HCV antibody-positive human patient was perfused with ice-cold Viaspan (Dupont Pharmaceutical) preservation solution and received on ice in Viaspan.
Precision-cut liver slices of ~200-250 μm thickness and 8 cm diameter were prepared and cultured in Waymouth's cell culture medium (Gibco, Inc.) that was supplemented with 10% fetal bovine serum and 10 mL/L Fungi-Bact at 37° C., and gassed with carbogen (95% $O_2$, 5% $CO_2$) at 0.75 liters/min Tissue slices were maintained in culture for 72 h. Cell culture medium containing test compound in solution was changed on a daily basis.
At appropriate times of liver slice incubation, liver slices and medium were collected for analysis of HCV RNA (tissue and medium) and nucleotide levels (NTP). All collected media and tissue slices were maintained in liquid $N_2$ until analysis.
Medium and tissue samples were analyzed for HCV RNA levels according to published procedures (Bonacini et. al., 1999) which utilize an automated, multicycle, polymerase chain reaction (PCR)-based technique. This assay has a lower limit of detection for HCV RNA of 100 viral copies/ml.

Analysis of Tissue NTPs: Frozen liver slices were disrupted by using a combination of ultrasound probe sonication, Branson Sonifier 450 (Branson Ultrasonics, Danbury, Conn.) and homogenization using a Dounce conical pestle in 200 μls of 10% (v/v) perchloric acid (PCA). After a 5 min centrifugation at 2,500×g, the supernatants were neutralized using 3 M KOH/3 M $KHCO_3$ and mixed thoroughly. The neutralized samples were centrifuged at 2,500 g for 5 min and NTP levels were determined by ion exchange phase HPLC (Hewlett Packard 1050) using a Whatman Partisil 5 SAX (5 μm, 4.6×250 mm) column Samples (50 μL) were injected onto the column in 70% 10 mM ammonium phosphate buffer and 30% 1 M ammonium phosphate buffer, both at pH 3.5 and containing 6% ethanol. Nucleoside triphosphates were eluted from the column using a linear gradient to 80% 1 M ammonium phosphate pH 3.5/6% ethanol buffer, at a flow rate of 1.25 mL/min and detected by UV absorbance (254 nm).

Example G

Tissue Distribution Following Oral Administration of Nucleoside Analogues and their Prodrugs The liver specificity of prodrug compounds 105, 107, and 110 are compared relative to their parent nucleoside, ribavirin, in liver and other organs that could be targets of toxicity.
Methods:
Ribavirin and their prodrugs are administered at 20 or 5 mg/kg (in terms of nucleoside equivalents) to fasted rats by oral gavage. Plasma concentrations of nucleoside are determined by HPLC-UV, and the liver and red blood cell (RBC) concentrations of the 5'-triphosphate of the nucleoside at 1 and 5 hours after dosing are measured by LC-MS using the standard ion-pairing chromatography method for triphosphate as similar as described in Example E.
Results:
The results are summarized in Table 1 and demonstrate the liver targeting of the ribavirin prodrugs by significantly higher Liver Targeting Index numbers. As a result, the prodrug compounds should have less chance to generate active form in RBC where the major side effect of ribavirin takes place. Although the liver NTP level of ribavirin is much higher at 1 hour after dosing, it quickly drops to a level similar to that of the prodrugs. The oral bioavailability of the prodrugs as a potential once a day drug can be optimized to achieve a liver NTP AUC level comparable to that of ribavirin currently given as twice a day.

TABLE 1

| Nucleoside [Prodrug] | Liver NTP concentration at 1 h (ng/g) | Liver NTP concentration at 5 h (ng/g) | Plasma Nucleoside concentration at 1 h/5 h (ng/mL) | Liver Targeting Index (Liver/Plasma) | RBC NTP concentration at 5 h |
|---|---|---|---|---|---|
| Ribavirin (20 mg/kg) | 40,600 | 3,647 | 1,531/286 | 26.5/12.7 | 757 |
| Compound 105 (20 mg/kg equiv) | 2,377 | 2,363 | 2.90/4.37 | 819/540 | ND |
| Compound 107 (20 mg/kg equiv) | 3,883 | 3,560 | 4.63/7.64 | 838/465 | ND |
| Compound 110 (5 mg/kg equiv) | ND | 1,529 | 2.12 (5 h) | 721 (5 h) | ND |

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A compound of Formula I:

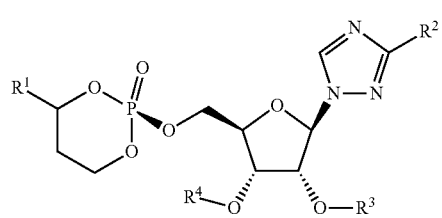

(I)

or a pharmaceutically acceptable salt thereof, wherein:

$R^1$ is an optionally substituted phenyl;

$R^2$ is

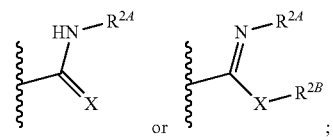

$R^{2A}$ is selected from the group consisting of H, a $C_1$-$C_6$ alkyl, a $C_1$-$C_6$ heteroalkyl, and a $C_1$-$C_6$ acyl;

$R^{2B}$ is selected from the group consisting of H, a $C_1$-$C_6$ alkyl, a $C_1$-$C_6$ heteroalkyl, and a $C_1$-$C_6$ acyl;

$R^3$ and $R^4$ are each independently selected from the group consisting of H, acyl, and heteroacyl; or $R^3$ and $R^4$ can be optionally linked to form a carbonyl; and X is O, S, or NH.

2. The compound of claim 1, wherein $R^1$ is selected from the group consisting of:

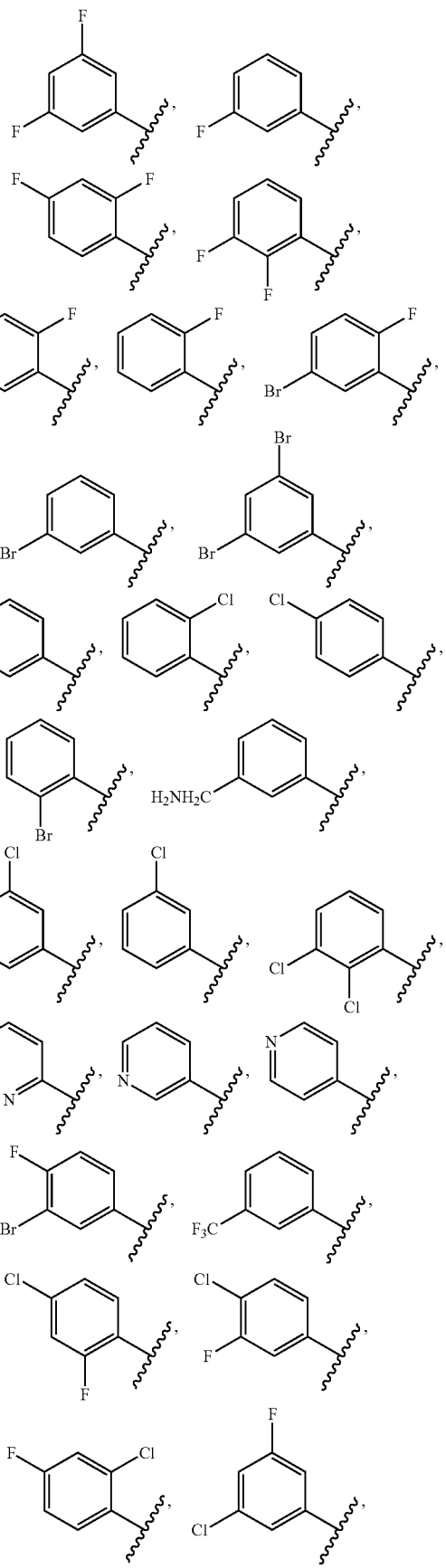

-continued

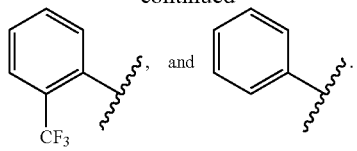

3. The compound of claim 2, wherein $R^2$ is

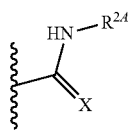

4. The compound of claim 3, wherein X is O.
5. The compound of claim 4, wherein $R^{2A}$ is selected from the group consisting of H and $C_1$-$C_6$ alkyl.
6. The compound of claim 5, wherein $R^3$ and $R^4$ are each H, or $R^3$ and $R^4$ can be optionally linked to form a carbonyl.
7. The compound of claim 2, wherein $R^2$ is

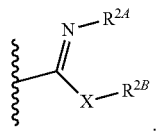

8. The compound of claim 7, wherein X is O.
9. The compound of claim 8, wherein $R^{2A}$ is of H.
10. The compound of claim 9, wherein $R^{2B}$ is $C_1$-$C_6$ alkyl.
11. The compound of claim 10, wherein $R^3$ and $R^4$ are each independently selected from the group consisting of H, acyl, and heteroacyl.
12. The compound of claim 1 selected from the group consisting of
2R-(3-Aminocarbonyl-1H-1,2,4-triazole)-5R-(4S-(3-chlorophenyl)-2-oxo-1,3,2-dioxaphosphorinanyloxymethyl)-3R,4R-dihydroxytetrahydrofuran,
2R-(3-Aminocarbonyl-1H-1,2,4-triazole)-5R-(4R-(3-chlorophenyl)-2-oxo-1,3,2-dioxaphosphorinanyloxymethyl)-3R,4R-dihydroxytetrahydrofuran,
2R-(3-Aminocarbonyl-1H-1,2,4-triazole)-5R-(4S-(3-chlorophenyl)-2-oxo-1,3,2-dioxaphosphorinan-2R-yloxymethyl)-3R,4R-dihydroxytetrahydrofuran,
2R-(3-Aminocarbonyl-1H-1,2,4-triazole)-4R-(4S-(3-chlorophenyl)-2-oxo-1,3,2-dioxaphosphorinan-2R-yloxymethyl)-7-oxo-3,6,8-trioxa-cis-bicyclo[3.3.0]octane,
2R-(3-Aminocarbonyl-1H-1,2,4-triazole)-5R-(4S-(3-chlorophenyl)-2-oxo-1,3,2-dioxaphosphorinan-2R-yloxymethyl)-3R,4R-diacetyloxytetrahydrofuran,
2R-(3-(1-Ethoxy-1-iminomethyl)-1H-1,2,4-triazole)-5R-(4S-(3-chlorophenyl)-2-oxo-1,3,2-dioxaphosphorinan-2R-yloxymethyl)-3R,4R-diacetyloxytetrahydrofuran,
2R-(3-Ethylaminocarbonyl-1H-1,2,4-triazole)-5R-(4S-(3-chlorophenyl)-2-oxo-1,3,2-dioxaphosphorinan-2R-yloxymethyl)-3R,4R-diacetyloxytetrahydrofuran, and
(2R,3R,4R,5R)-2-(3-Carbamoyl-1H-1,2,4-triazol-1-yl)-5-((((2R,4S)-4-(3-chlorophenyl)-2-oxido-1,3,2-dioxaphosphinan-2-yl)oxy)methyl)tetrahydrofuran-3,4-diyl dipropionate, or a pharmaceutically acceptable salt thereof.
13. The compound of claim 1, wherein $R^1$ is phenyl substituted with halogen.
14. A pharmaceutical composition comprising the compound of claim 1, and a pharmaceutically acceptable carrier.
15. A method of treating a viral infection comprising administering an effective amount of a compound claim 1 to a subject in need thereof.
16. The method of claim 15, further comprising administering an effective amount of a second therapeutic agent in combination with the compound claim 1 to the subject in need thereof, wherein the second therapeutic agent is selected from the group consisting of thymosin alpha-1, interferon-λ, an inhibitor of HCV protease, an inhibitor of HCV NS5A replication complex, an inhibitor of HCV NS5B polymerase, an inhibitor of HCV helicase, a cyclophilin inhibitor, an inhibitor of inosine monophosphate dehydrogenase, interferon-α, and pegylated interferon-α.
17. The method of claim 15, wherein the viral infection is an infection of the liver.
18. The method of claim 15, wherein the viral infection is HCV.
19. A method of inhibiting viral replication in a cell comprising contacting the cell with the compound of claim 1.
20. The method of claim 19, wherein the viral replication is HCV replication.
21. The method of claim 19, further comprising contacting the cell with a second antiviral agent selected from the group consisting of thymosin alpha-1, interferon-λ, an inhibitor of HCV protease, an inhibitor of HCV NS5A replication complex, an inhibitor of HCV NS5B polymerase, an inhibitor of HCV helicase, a cyclophilin inhibitor, an inhibitor of inosine monophosphate dehydrogenase, interferon-α, and pegylated interferon-α.
22. The method of claim 19, wherein the cell is a hepatocyte.

* * * * *